United States Patent [19]

Janata

[11] Patent Number: 5,667,470
[45] Date of Patent: Sep. 16, 1997

[54] APPARATUS AND METHOD FOR USING LISTENER FEEDBACK TO DETERMINE THE NATURE OF SOUND STIMULI PRESENTED TO THE LISTENER

[75] Inventor: Petr Janata, Eugene, Oreg.

[73] Assignee: Jiri Janata, Richland, Wash.

[21] Appl. No.: 193,224

[22] Filed: Feb. 8, 1994

[51] Int. Cl.⁶ .................................................. A61M 21/00
[52] U.S. Cl. ...................................................... 600/28
[58] Field of Search ................ 600/26–28; 128/731–32, 128/905

[56] References Cited

U.S. PATENT DOCUMENTS

| | | | |
|---|---|---|---|
| 4,883,067 | 11/1989 | Knispel et al. | 600/28 |
| 5,267,942 | 12/1993 | Saperston | 600/28 |
| 5,282,475 | 2/1994 | Urbach et al. | 128/731 |
| 5,365,939 | 11/1994 | Ochs | 128/731 |

Primary Examiner—John P. Lacyk
Attorney, Agent, or Firm—Thorpe, North & Western, L.L.P.

[57] ABSTRACT

A method for using patient feedback to influence presentation of sound stimuli during music therapy comprises presenting a first stimulus to induce a predicted degree of expectancy fulfillment, detecting brain electrical activity generated by the patient in response thereto, determining values of certain parameters of the brain electrical activity, comparing the parameters to a classification library to determine the actual degree of expectancy fulfillment or violation, calculating a correction factor based on the difference between the predicted and actual degrees of expectancy fulfillment or violation, determining the configuration of a second stimulus taking into account the correction factor, and arranging and presenting the second stimulus to the patient. Apparatus for carrying out the method comprises an arrangement of readily available hardware and software components.

19 Claims, 5 Drawing Sheets

PROPOSED

PROPOSED

APPARATUS AND METHOD FOR USING LISTENER FEEDBACK TO DETERMINE THE NATURE OF SOUND STIMULI PRESENTED TO THE LISTENER

FIELD OF THE INVENTION

The present invention concerns apparatuses and methods for monitoring and influencing a person's mood, especially apparatuses and methods using music or sound as the sole or primary stimulus of the person.

BACKGROUND OF THE INVENTION

A music therapist desires to instill various cognitive states in his patients, each according to their individual needs. He may wish to relax one patient, but agitate another; energize one, but frustrate another; etc. Additionally, it often is desired to instill a variety of changing cognitive states in a patient during a single session. All this is accomplished by choosing particular sequences of music to play to the patient which facilitate the desired mood.

It can be realized from common experience that different types of music evoke differing moods in the listener, ranging from agitation and displeasure, to pleasure, relaxation, and even boredom. Music theory has quantified this intuitive knowledge by identifying the parameters that define different types of music and their usual effect on the listener. A therapist attempts to apply this knowledge to clinical patients by varying one or more parameters to evoke a particular desired response.

An important quantifiable parameter of music is the degree to which it fulfills or violates the expectations of the patient. By means of the rules of melody, harmony, and rhythm in a general musical system, such as western tonal music, certain musical stimuli are more likely than others to follow a given musical sequence. Given a specific musical context, one can categorize the next musical stimulus in order of probability of occurrence, taking into account, of course, the specific styles of the music. What constitutes a major expectancy violation in one style of music might not be as significant an expectancy violation in another. One can therefore choose a particular type of musical stimulus from the list of possible stimuli whose probability of occurrence matches the value of the desired expectancy state. Expectancies in music are principally generated along harmonic, melodic and rhythmic dimensions. All these aspects can be expressed in separate probability distributions and incorporated into the creation of an overall auditory stimulus.

Music that generates an expectancy in the listener and then violates that expectancy creates tension, and is thus emotionally more challenging and potentially more distressing, than music which fulfills the expectancy. Thus, there are expectancy differences between dissonant music, which strays from the usual chord structures; melody sequences to which a listener in our society has become accustomed, and melodious and harmonious music, which retains simple and expected structures and sequences.

Given a series of musical stimuli, the music therapist can, from the principles of music theory and from the styles of music a person has been exposed to, predict the approximate expectancy value of a particular future stimulus, the expectancy value being the degree to which the listener perceives the stimulus as consonant with (or, conversely, deviant from) what he expects to hear. Thus the therapist can predict what emotional effect that musical stimulus will have on his patient. The therapist can therefore choose between different types of music to select the one that will evoke an emotional state in the patient most closely approximating the desired therapeutic emotional state. There exists, of course, a wide variety of musical choices for use in therapy, including classical, jazz, rock, hymns, and other generally available selections, as well as a growing body of music that is written specifically for therapeutic ends.

Though music therapy has proven to be of significant value, therapists are limited by the inexact science of predicting and assaying a listener's reaction to a particular musical sequence. A listener's actual reaction to a musical sequence almost invariably differs to some extent from the predicted reaction. In terms of expectancies, the degree of the actual expectancy fulfillment or violation differs from the predicted value. This is due to our incomplete understanding of the effect of numerous variables on expectancy violation/fulfillment, and in large part to the varying effects a single musical sequence will have on different individuals due to their distinct backgrounds and musical experiences. There exists, therefore, room for improvement in the efficacy of music therapy treatment.

OBJECTS AND SUMMARY OF THE INVENTION

It is therefore an object of the present invention to overcome the shortcomings of prior art music therapy apparatuses and methods.

It is a further object of the invention to provide a method of altering a subject's cognitive state in a predetermined manner with sound stimuli, using feedback from the subject to determine the degree of correlation between the predicted cognitive state and the actual cognitive state, and to construct subsequent sound stimuli accordingly.

It is a further object of the invention to provide an apparatus for carrying out the above method using generally available electronic components.

In accordance with a first aspect of the invention, a method of using feedback from a subject to analyze and present to the subject sound stimuli adapted to induce a predetermined response in the subject comprises the steps of presenting a first sound stimulus to the subject during a first time period, said first sound stimulus being adapted to induce a predicted response in the subject, determining the actual response of the subject to the first sound stimulus, and comparing the predicted and actual responses to the first stimulus. A second sound stimulus to be presented to the subject during a second time period is determined, taking into account the difference, if any, between the predicted and actual responses to the first stimulus.

In accordance with a second aspect of the invention, an apparatus for using feedback to influence sound stimuli presented to a subject in music therapy comprises detection means for detecting electrical signals from the brain, e.g., an EEG of the subject during presentation of sound stimuli during a first time period, said sound stimuli being adapted to induce an EEG predicted response in the subject, and a digital converter operatively connected to the detection means for digitizing the signals. Any method of analyzing the EEG recorded at scalp electrodes can be utilized to assess the degree of expectancy violation. For example, a processor for analyzing spectral and/or time domain parameters can be connected to the digital converter. The processor Fourier transforms digitized signals into component sine waves, and a pattern recognition processor, operatively connected to the spectral analysis processor, classifies predetermined parameters of the component sine waves thereby determining the subject's actual response to the presented stimuli. (The discussion of transformation uses Fourier transformations as an example only. The processor can use any method for mathematically transforming the digitized signals into component basis functions. Those skilled in the art will recognize several different ways in which this can be done.)

A stimulus configuration processor operatively connected to a pattern classifier determines a suitable sound configuration to be presented to the subject in a second time period subsequent to the first time period based on a comparison between the subject's predicted and actual responses to the stimuli presented in the first time period, and a stimulus presentation processor operatively connected to the sound (stimulus) configuration processor gives the sound configuration a suitable temporal arrangement. While discussed as separate elements, it is possible to merge the stimulus configuration and stimulus presentation processors into one unit. A sound synthesizer operatively connected to the stimulus presentation processor generates sounds according to the temporal arrangement created by the stimulus presentation processor, and a speaker operatively connected to the sound synthesizer presents the sounds generated by the sound synthesizer to the subject.

Specifically, and in a preferred embodiment, a method of adjusting musical stimuli presented to a music therapy patient in real time for achievement of a desired cognitive state comprises the steps of presenting a first musical stimulus to the patient during a first time period to cause first predetermined predicted degree of expectancy fulfillment, detecting brain electrical activity generated by the patient during the first time period, and determining the values of certain pre-determined parameters in the brain waves and generating a pattern vector comprising those values. The pattern vector is compared to a classification library of pattern vectors having corresponding degrees of expectancy fulfillment. The library pattern vector most similar to the pattern vector is found and the actual degree of expectancy fulfillment is thereby determined. The actual degree of expectancy fulfillment is compared to the first predicted degree of expectancy fulfillment and a first correction factor based on said comparison is calculated. The configuration of a second musical stimulus is determined based on a second desired degree of expectancy fulfillment and the correction factor. The second musical stimulus is arranged with the desired degree of expectancy fulfillment according to the rules governing the particular music style and presented to the patient during a second time period.

BRIEF DESCRIPTION OF THE DRAWINGS

These and other objects, aspects, and embodiments of the present invention will be described with reference to the attached drawings figures, of which.

DETAILED DESCRIPTION OF THE INVENTION

Figure 1:
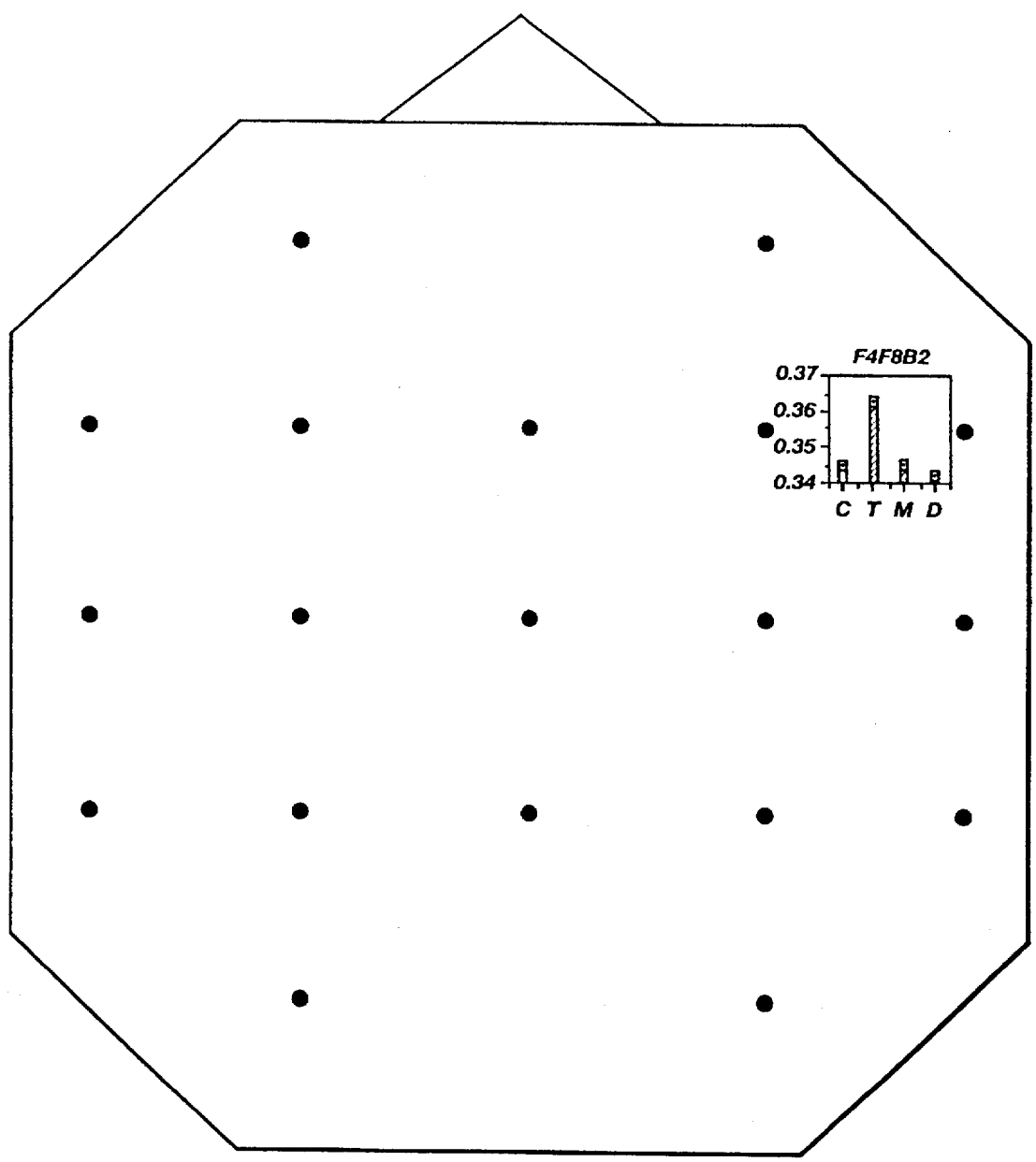
FIG. 1 is an example graph of a coherence parameter of EEG signals from two electrodes which are sensitive to expectancy fulfillment, the coherence being measured between the two electrodes adjacent the graph.

It has been found that the cognitive state of a subject listening to music, including his emotional reactions to the music, can be ascertained by analyzing his electroencephalogram (EEG). A person's EEG is a record of his brain's electrical activity, recorded at multiple electrode sites on the person's head. The EEG signal waveform at any given electrode can be analyzed by breaking down the complex signal into its component sine wave frequencies through Fourier analysis. Additionally, it has been found that other brain activity monitors also work with the invention, such as ERP's (untransformed EEG signals).

The component waves are mathematically described by giving values to certain parameters, including amplitude and frequency of a particular component wave, and coherence (similarity) between component wave spectra of any two different electrodes. For example, local coherence is measured between adjacent electrodes, and interhemispheric coherence is measured between homologous electrode sites above the two hemispheres. As will be apparent to those skilled in the art, multiple combinations and numbers of electrodes may be used.

Different cognitive states will generate different waveforms, which in turn have different component spectra amplitude and coherence values. These values are applied to measure to what degree a music therapy patient (or any listener) perceives a given sequence of musical or sound stimuli as fulfilling or violating his expectations.

Hundreds of different amplitude and coherence parameters result from a standard 32 or 64 electrode EEG attachment to a subject's head. In fact, 128 electrode attachments have been developed and can be used with the invention. Out of these parameters, the therapist can determine which are most sensitive to expectancy violation and fulfillment in predictable ways, both generally and for each individual patient, and use these sensitive parameters to determine the actual degree to which the musical expectancies have been violated or fulfilled. This is done by creating a reference classification library of parameter patterns which indicate a sensitivity to expectancy violations produced by a suite of musical sequences in a variety of styles. When a patient's EEG signals are subsequently monitored, the monitored set of parameters is extracted, measured, and compared against the classification library to find the reference parameter measurement set that most closely approximates the actual measurement. The actual cognitive state of the patient can then be determined by noting the cognitive state corresponding to that classification.

A musical expectancy has multiple determinants. Consequently, what constitutes a major expectancy violation in one style of music might not be as gross an expectancy violation in another. Likewise, what is perceived as an expectancy violation is likely to vary between subjects. Specific genres of music, therefore, can be analyzed and described in terms of musical event probabilities (expectancies), so that the classification libraries are tailored to a specific style of music. Similarly, the trends and patterns in actual expectancy violations experienced by the subjects can be used to modify the initial tables predicting degrees of expectancy violations, so that the predictions become more precise.

Figure 2:
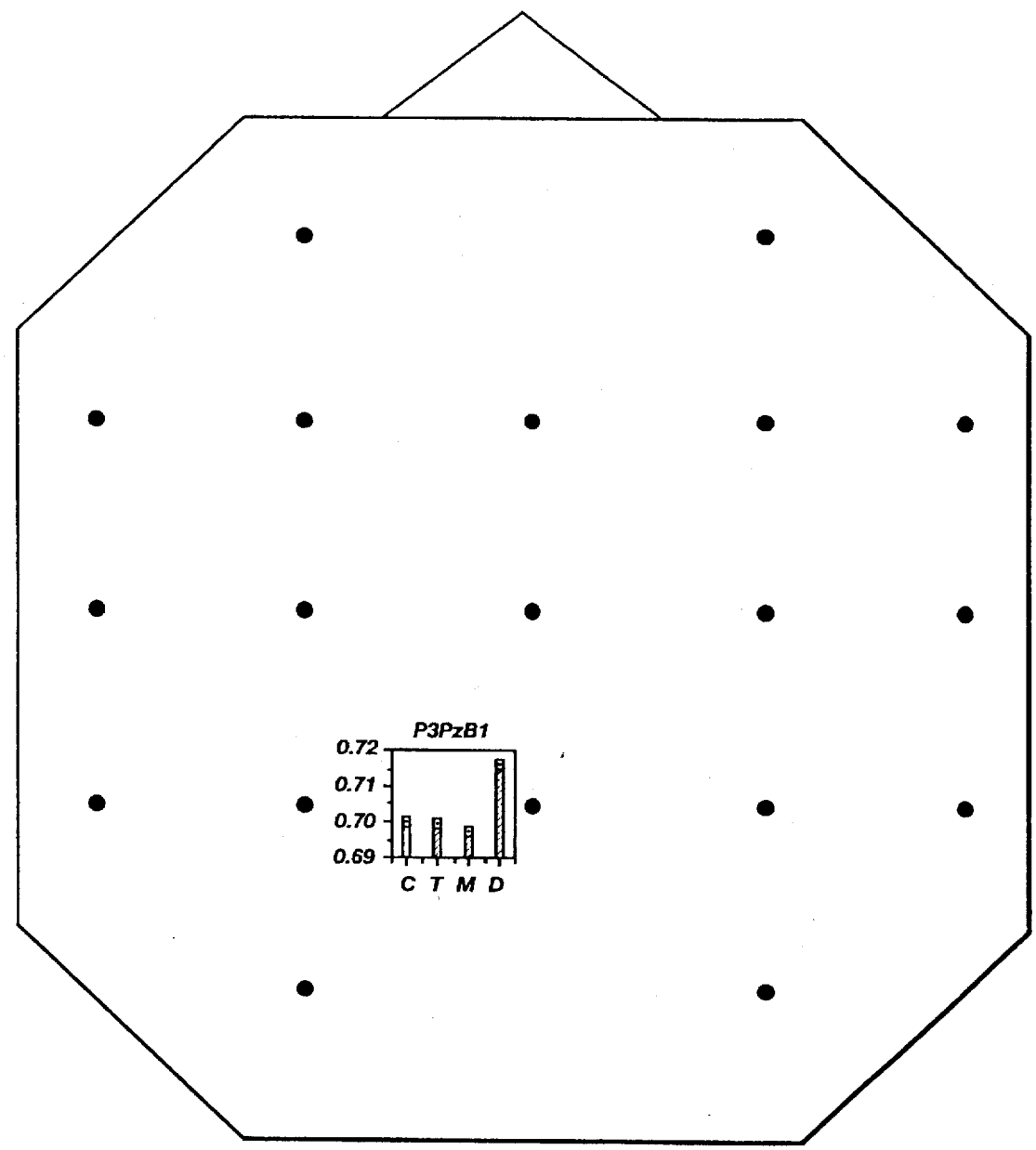
FIG. 2 is another example of a coherence parameter sensitive to expectancy violation taken between two electrodes.
Figure 3:
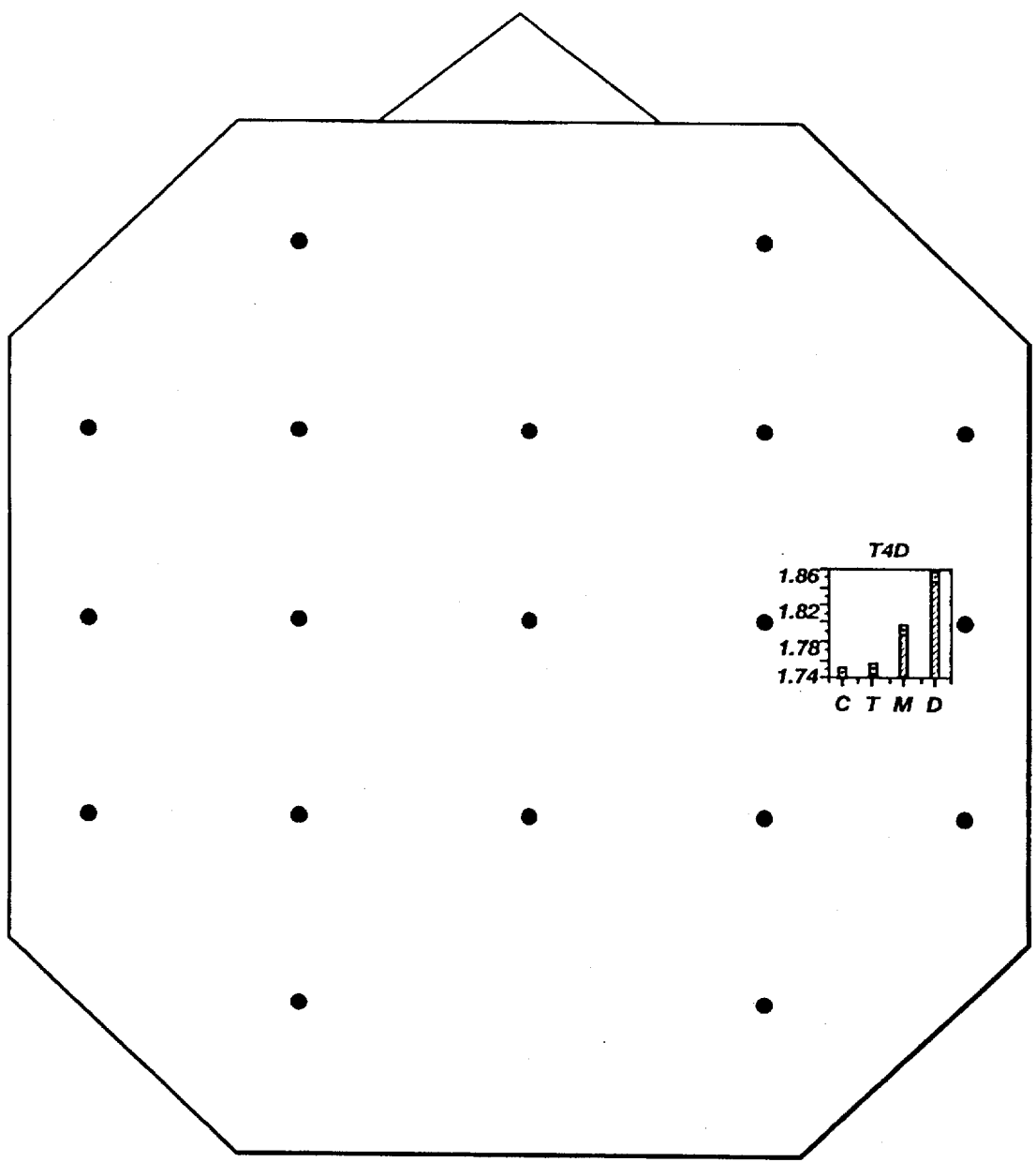
FIG. 3 is an example of an amplitude parameter taken from a single electrode which is sensitive to expectancy violation and fulfillment.

FIGS. 1 to 3 illustrate examples of parameters sensitive to expectancy violation and fulfillment. FIG. 1 shows the coherence between two electrodes at locations F4 and F8 in the beta2 frequency band (18.5–24.0 Hz), the location designations being generally known in the art as part of the International 10–20 Electrode System. The band designations are common in the literature. The bar graph C illustrates the coherence between the electrodes during the segment of music generating the expectancy. The bar graph T illustrates the coherence between the electrodes when the expectancy is fulfilled in the best possible way, the graph M illustrates their coherence when the expectancy is fulfilled in a mediocre way, and the graph D illustrates their coherence when the expectancy is fulfilled in the worst possible way, i.e., completely violated. It can be seen that the coherence between the electrodes increased significantly in response to the best possible expectancy fulfillment, and is thus a suitably sensitive parameter for use with the invention.

FIG. 2 shows another sensitive parameter: the coherence between two electrodes at locations P3 and Pz in the beta1 frequency band (13.0–18.0 Hz). In this case, the coherence between the electrodes greatly increased in response to the worst possible expectancy fulfillment.

FIG. 3 shows yet another sensitive parameter: The amplitude of the electrode T4 in the delta frequency band (1.5–3.5 Hz). This parameter exhibited increased magnitude proportionate to the degree of expectancy violation.

It has been found that the measurement and comparison of 10 to 15 sensitive parameters such as those illustrated in FIGS. 1 to 3 is sufficient to accurately ascertain the degree to which the patient perceives a given musical or sound sequence as fulfilling or violating his expectations. However, a larger set of parameters will provide a more precise classification. Given the current state of the art, it is relatively simple to classify even hundreds of parameters in real time. A general classification library can initially be used for a particular patient, which then can be modified and made more accurate according to the patient's individual measurements, or an individualized library can be created at the outset. No one person will exhibit exactly the same parameter sensitivity as another.

The invention comprises a method of modifying the sound stimuli given to a patient in real time based on real time feedback from the patient of how precisely the patient's reactions to the sound stimuli, specifically with regard to expectancy fulfillment, correspond to the predicted reactions. If the degree of actual expectancy fulfillment differs from the predicted degree, the stimulus is modified in real time to take into account the discrepancy and to supply a stimulus which more precisely corresponds to the desired expectancy state.

Figure 4:
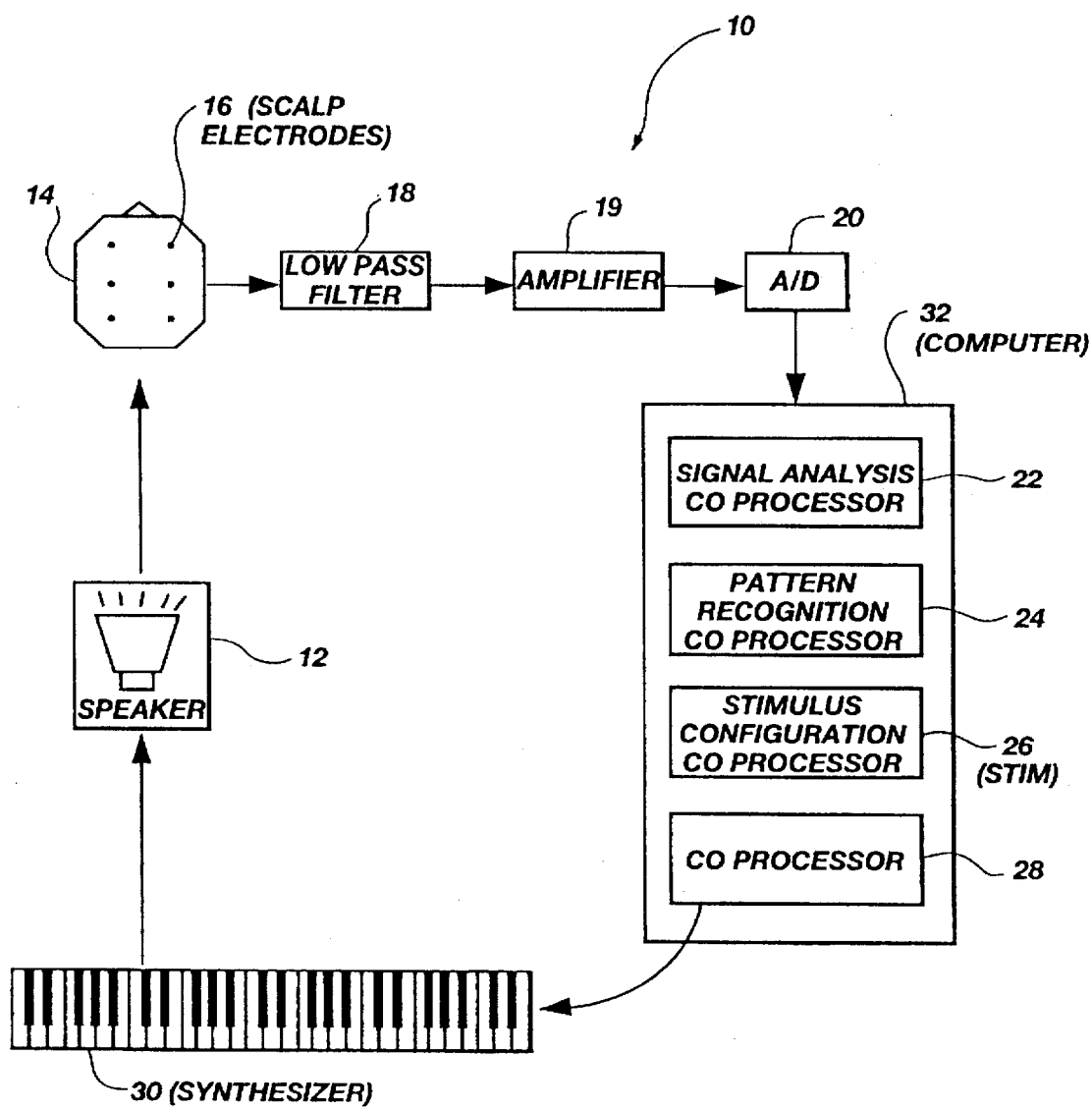
FIG. 4 is a schematic illustration of an apparatus according to the invention for providing expectancy fulfilling and violating feedback in real time.
Figure 5:
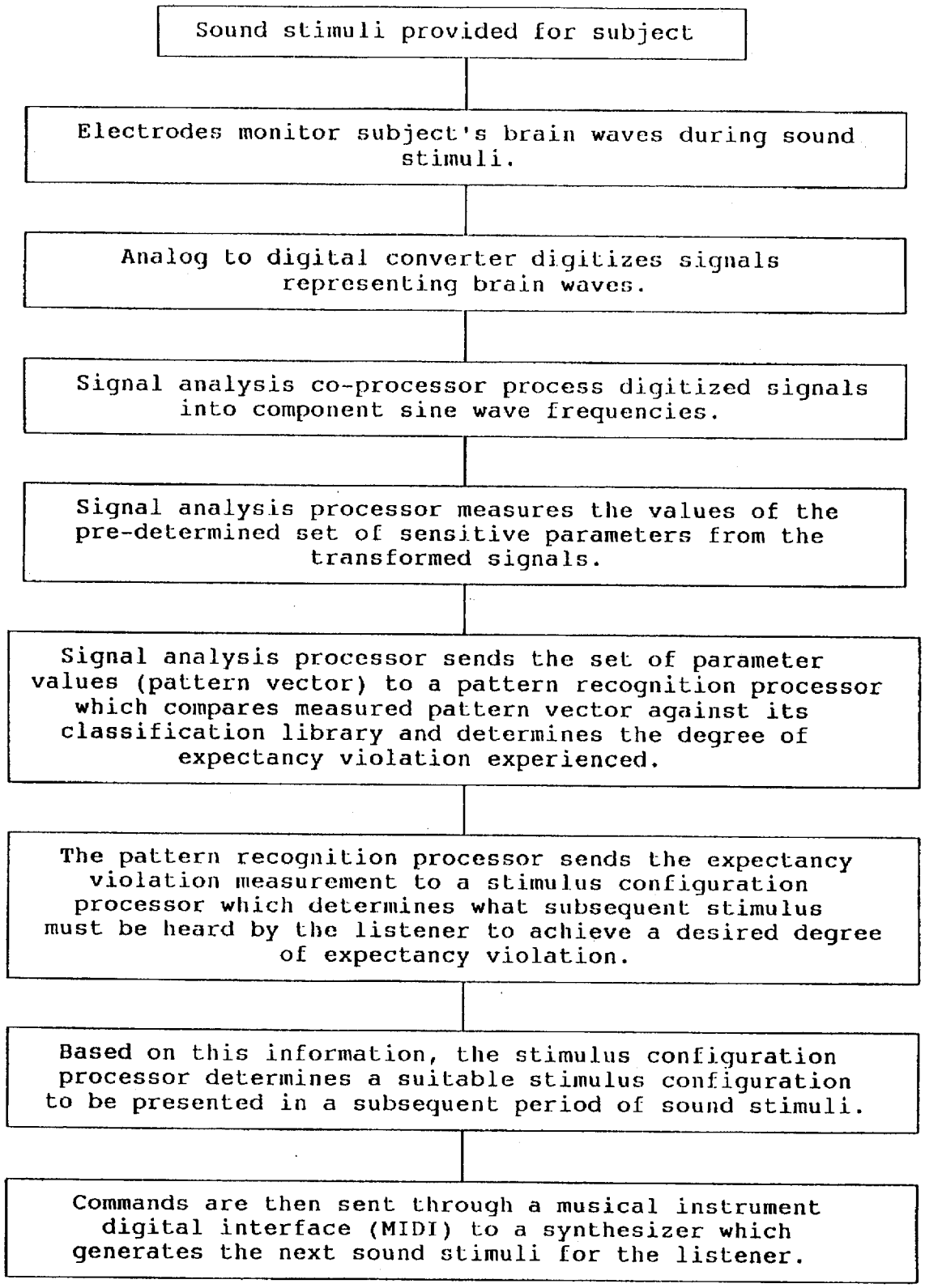
FIG. 5 shows a flowchart summarizing a preferred embodiment of the invention.

Referring now to FIG. 4, an apparatus 10 according to the invention is shown schematically. The apparatus 10 monitors a subject's reaction to music or sound stimuli and creates or modifies subsequent stimuli in real time based on the subject's reaction. Speakers 12 provide sound or musical stimuli to a listener 14. A plurality of non-invasive EEG scalp electrodes 16, such as those manufactured by Grass Corp., attach to the head of the listener for detection of EEG signals. It has been found that 32 or more electrodes are preferable, each electrode comprising a separate channel for signal manipulation and processing. The more electrodes there are, the more precise the pattern which is to be classified. A low-pass filter 18 receives the signals from the electrodes 16 and removes noise. Since human EEG signals range from 0 Hz up to at least 90 Hz, a cutoff of 150 Hz for the filter 18 is acceptable. An amplifier 19 receives the filter signals and amplifies them between 10,000 and 100,000 times. Combination filter/amplifiers are commercially available from Grass Corp. or Nicoh/Kohden Corp.

An analog to digital (A/D) converter 20 receives the amplified signals and digitizes them. Many suitable A/D converters are commercially available as boards which can be added to personal computers or workstations, such as those produced by National Instruments. Digitization at 128 samples per second with 12-bit precision has been found to be sufficient for operation of the apparatus 10. A signal analysis co-processor 22 receives the digitized signals and computes a fast-Fourier transform (FFT) on the waveform to separate it out into its component sine wave frequencies. Intel corporation currently produces high-speed processors capable of Fourier transforming 1024 point waves (i.e., waves consisting of 1024 digitized samples) in 1 millisecond. This type of processor will therefore be able to Fourier transform the 128 point digitized waves of all 32 electrode channels in less than 4 milliseconds. It is anticipated that the simplest apparatuses built according to the invention will provide stimulus updates every one or two seconds, allowing ample time for all necessary calculations. This update period may, of course, be varied according to accuracy requirements or hardware limitations.

After completing the Fouriera transform, the signal analysis processor 22 measures the values of the predetermined set of sensitive parameters from the transformed signals. In the case of the spectral amplitude parameter, the value is merely extracted from the power spectrum at the appropriate frequency, while in the case of coherence between electrodes, the value must be calculated. In the case of time domain information, a desired temporal window of untransformed EEG from all channels is used as a pattern vector. The processor 22 then sends the set of parameter values, or pattern vector, to a pattern recognition processor 24, comparing the measured pattern vector against its classification library, which classifies it by determining which library pattern vector most closely approximates the measured vector, and determines the degree of expectancy violation the listener 14 has experienced.

The field of pattern recognition is constantly evolving; those skilled in the art will be able to arrive at new algorithms which increase speed and accuracy of the classification process. The processor 24 can use any suitable algorithm now known in the art or available in the future.

The processor 24 sends the expectancy violation measurement to a stimulus configuration processor 26, which determines what subsequent stimulus must be heard by the listener 14 to achieve a desired degree of expectancy violation. This is done by using the preceding series of expectancy state predictions, the preceding series of actual expectancy states achieved, the ratio of desired expectancy violations to desired expectancy fulfillments (a good index of how emotionally disturbing the music is), the preceding stimulus sequence, and general rules governing the musical style.

In a preferred embodiment, if an expectancy has been fulfilled more than was predicted, the following stimulus is selected to be one which is less probable, i.e., more of a predicted expectancy violation, than would have been presented had the actual degree of fulfillment been equal to the predicted degree of fulfillment. Conversely, if an expectancy has been violated more than was predicted, the following stimulus is selected to be one which is more probable, i.e., more of a predicted expectancy fulfillment, than would have been presented had the actual degree of fulfillment been equal to the predicted degree of fulfillment. For example, the degree of expectancy fulfillment of a stimulus may be scaled from 0 to 1, 0 being a complete expectancy violation and 1 being a complete expectancy fulfillment. If the target expectancy state for the stimulus presented during the previous update period was 0.5 but the actual expectancy state, as determined by the pattern recognition processor 24, was 0.4, the comparison between the predicted and actual effects of the previous stimulus reveals that the stimulus did not produce the predicted effect but was off by 0.1. Based on this information, the stimulus configuration processor 26 determines a suitable stimulus configuration to be presented over the next update period which is predicted to produce an expectancy state of 0.6 in order to achieve a desired state of 0.5, i.e., it incorporates a correction factor of 0.1.

Suitable stimulus configuration processor software and algorithms exist in the art which can be used with the present invention. The correction factor can be incorporated into the stimulus configuration based on standard techniques in light of this disclosure. The stimulus configuration comprises an array of input information governing the musical stimuli to be played over the course of the next update period, e.g., one second.

Based on the results of its calculations, the processor 26 determines a suitable configuration (in terms of musical events in time) for the next musical stimulus to be presented to the listener, and then sends musical instrument digital interface (MIDI) commands to a synthesizer 30 which generates sounds accordingly, and presents them to the listener through the speakers 12.

While discussed above as a linear function, any given correction factor need not be based on the immediately prior expectancy violation. For example, if two musical stimuli have been presented to a subject and a third is desired, a second correction factor for determining the third stimulus can be based on the expectancy violations of the first stimulus, the second stimulus, or both. If a fourth stimulus is desired, a third correction factor can be based on the expectancy violation of the first, second or third stimulus, or any combination thereof.

A computer 32 containing the A/D converter 20, co-processors 22, 24, 26, and 28, and accompanying circuitry is provided for overall control of the process and for a user interface, allowing the therapist to monitor progress and make changes as needed. This allows the user to arrange the sound configuration through a computer-generated rule-based music composition program.

The apparatus has been described with four co-processors as the preferred embodiment based on speed limitations of currently available hardware. Since the calculations are made in real time, sufficiently rapid instrumentation must be used to make the calculations. Those skilled in the art will appreciate, however, that other hardware configurations can be used with similar results provided they are able to make the necessary calculations within the update period desired. Similarly, the algorithms described herein are only one method in which the actual degree of expectancy violation or fulfillment can be determined and subsequently used to create or tailor a future stimulus for maximum desired effect on the patient.

I claim:

1. A method of adjusting musical stimuli presented to a music therapy patient in real time for achievement of a desired cognitive state comprising the steps of:

presenting a first musical stimulus to the patient during a first time period to cause a first pre-determined predicted degree of expectancy fulfillment;

detecting the brain-electrical activity generated by the patient during the first time period;

determining the values of certain pre-determined parameters in the brain waves and generating a pattern vector comprising those values;

comparing the pattern vector to a classification library of pattern vectors having corresponding degrees of expectancy fulfillment, finding the library pattern vector most similar to the pattern vector and thereby determining the actual degree of expectancy fulfillment;

comparing the actual degree of expectancy fulfillment to the first predicted degree of expectancy fulfillment and calculating a correction factor based on said comparison;

determining the configuration of a second musical stimulus based on a second predicted degree of expectancy fulfillment and the correction factor; and arranging the second musical stimulus according to the configuration and presenting it to the patient during a second time period.

2. The method of claim 1 wherein the correction factor comprises the difference between the degree of first predicted expectancy fulfillment and actual expectancy fulfillment.

3. The method of claim 2 wherein the correction factor is added to the second predicted degree of expectancy fulfillment, resulting in a third predicted degree of expectancy fulfillment, the second musical stimulus being configured to achieve the third predicted degree of expectancy fulfillment.

4. The method of claim 1 further comprising:

detecting the brain-electrical activity generated by the subject during the second time period;

determining the values of certain pre-determined parameters in the brain waves and generating a pattern vector comprising those values;

comparing the pattern vector to a classification library of pattern vectors having corresponding degrees of expectancy fulfillment, finding the library pattern vector most similar to the pattern vector and thereby determining the actual degree of expectancy fulfillment;

comparing the actual degree of expectancy fulfillment to a prior predicted degree of expectancy fulfillment and calculating a second correction factor based on said comparison;

determining the configuration of a third musical stimulus based on a third predicted degree of expectancy fulfillment and the second correction factor; and arranging the third musical stimulus according to the configuration and presenting it to the patient during a third time period.

5. The method of claim 1 wherein the second correction factor comprises a function of at least one prior expectancy violation level.

6. An apparatus for using feedback to influence sound stimuli presented to a subject in music therapy comprising:

detection means for detecting electrical signals from the brain of the subject during presentation of sound stimuli during a first time period;

analog to digital (A/D) converter means operatively connected to the detection means for digitizing the signals;

processor means operatively connected to the digital converter means for (a) transforming and classifying the signals and determining the subject's actual response to the presented stimuli, (b) determining a suitable sound configuration to be presented based on the predicted and actual response to the stimuli presented, and (c) giving the sound configuration a suitable temporal arrangement; and sound synthesizer means operatively connected to the processor means for generating sound stimuli according to the temporal arrangement created by the processor means, and wherein sound stimuli presented during said first time period is adapted to induce a predicted response in the subject.

7. The apparatus of claim 6 wherein the processor means comprises:

a pattern recognition processor means operatively connected to the digital converter means for classifying predetermined parameters of the signals and thereby determining the subject's actual response to the presented stimuli.

8. The apparatus of claim 6 wherein the processor means comprises stimulus configuration processor means for determining a suitable sound configuration to be presented to the subject in a second time period subsequent to the first time period, based on comparison between the subject's predicted and actual responses to the stimuli presented in the first period; and stimulus presentation means for giving the sound configuration a suitable temporal arrangement.

9. Apparatus for using feedback to influence sound stimuli presented to a subject in music therapy comprising:

sound generation means for generating sound stimuli being adapted to induce a predicted response in the subject during a first time period;

detection means for detecting electrical signals from the brain of the subject during presentation of the sound stimuli during said first time period;

analog to digital (A/D) converter means operatively connected to the detection means for digitizing the signals;

pattern recognition processor means operatively connected to the digital converter means for classifying pre-determined parameters of the signals and thereby determining the subject's actual response to the presented stimuli;

stimulus configuration processor means operatively connected to the analog to digital converter means for determining a suitable sound configuration to be presented to the subject in a second time period subsequent to the first time period, based on a comparison between the subject's predicted and actual responses to the stimuli presented in the first period;

stimulus presentation processor means operatively connected to the digital converter means for giving the sound configuration a suitable temporal arrangement;

sound synthesizer means operatively connected to the stimulus presentation processor means for generating sounds according to the temporal arrangement created by the stimulus presentation processor means; and speaker means operatively connected to the sound synthesizer means for presenting the sounds generated by the sound synthesizer means to the subject.

10. The apparatus of claim 9 wherein the detection means comprises a series of electrodes adapted to be non-invasively attached to the subject's head for detection of electroencephalogram signals.

11. The apparatus of claim 9 wherein the detection means comprises a series of electrodes adapted to be non-invasively attached to the subject's head for detection of ERP signals.

12. The apparatus of claim 9 further comprising a signal analysis processor operatively disposed between the digital converter means and the pattern recognition processor means for mathematically transforming the digitized signals into component basis functions.

13. The apparatus of claim 12 wherein the detection means comprises a series of electrodes adapted to be non-invasively attached to the subject's head for detection of electroencephalogram signals.

14. The apparatus of claim 12 wherein the detection means comprises a series of electrodes adapted to be non-invasively attached to the subject's head for detection of ERP signals.

15. The apparatus of claim 9 wherein the analog to digital converter means comprises a converter digitizing at least 128 samples per second with at least 12-bit precision.

16. The apparatus of claim 9 further comprising a low-pass filter operatively connected to the detection means for removing noise from the electric signals from the brain of the subject.

17. The apparatus of claim 16 further comprising an amplifier operatively connected to the low-pass filter for amplifying the signals.

18. The apparatus of claim 9 wherein the stimulus presentation processor gives a temporal arrangement to the sound configuration through a computer-generated neural network or rule-based music composition program.

19. The apparatus of claim 9 wherein the digital converter, spectral analysis processor, pattern recognition processor, stimulus configuration processor, and stimulus presentation processor are contained in a computer adapted to provide a user interface.

\* \* \* \* \*